(12) United States Patent
Wang

(10) Patent No.: US 8,594,780 B2
(45) Date of Patent: Nov. 26, 2013

(54) METHOD FOR ANALYZING THE STRUCTURE OF AN ELECTRICALLY CONDUCTIVE OBJECT

(76) Inventor: Wei Wang, Leicester (GB)

( * ) Notice: Subject to any disclaimer, the term of this patent is extended or adjusted under 35 U.S.C. 154(b) by 655 days.

(21) Appl. No.: 12/451,944

(22) PCT Filed: Jun. 6, 2008

(86) PCT No.: PCT/GB2008/001982
§ 371 (c)(1),
(2), (4) Date: Jun. 5, 2010

(87) PCT Pub. No.: WO2008/149125
PCT Pub. Date: Dec. 11, 2008

(65) Prior Publication Data
US 2010/0268109 A1    Oct. 21, 2010

(30) Foreign Application Priority Data
Jun. 7, 2007   (GB) .................................. 0710949.9

(51) Int. Cl.
*A61B 5/00* (2006.01)
(52) U.S. Cl.
USPC ........................................................ 600/547
(58) Field of Classification Search
USPC .................... 600/425, 547; 378/21
See application file for complete search history.

(56) References Cited

U.S. PATENT DOCUMENTS 6,856,824 B1    2/2005   Wang et al.

FOREIGN PATENT DOCUMENTS

WO    WO 96/12439    5/1996
WO    WO 00/12005    3/2000

OTHER PUBLICATIONS

P.M. Record, et al; "Multifrequency Electrical Impedance Tomography;" Clinical Physics and Physiological Measurement, Institute of Physics Publishing, Bristol, Great Britain; vol. 13, No. Suppl. A; Jan. 1, 1992; pp. 67-72.
E.T. Macadams, et al.; "Problems in Equivalent Circuit Modelling of the Electrical Properties of Biological Tissues;" Bioelectrochemistry and Bioenergetics; vol. 40, Aug. 31, 1996; pp. 147-152.

*Primary Examiner* — Max Hindenburg
(74) *Attorney, Agent, or Firm* — Ware, Fressola, Maguire & Barber LLP

(57) ABSTRACT

A method for analyzing the structure of an electrically conductive object, the method comprising the steps of: (i) obtaining electrical impedance data for the object over a range of frequencies; (ii) analyzing the obtained electrical impedance data using a transfer function of an assumed electrical model to determine a plurality of electrical impedance properties for the object; (iii) constructively combining selected ones of the determined plurality of electrical impedance properties to provide at least one parametric impedance value for the object; and (iii) imaging one or more of the determined parametric impedance values.

20 Claims, 2 Drawing Sheets

METHOD FOR ANALYZING THE STRUCTURE OF AN ELECTRICALLY CONDUCTIVE OBJECT

CROSS REFERENCE TO RELATED APPLICATIONS

This application is the U.S. National Stage of International Application Number PCT/IB08/001,982 filed on Jun. 6, 2008 which was published in English on Dec. 11, 2008 under International Publication Number WO 2008/149125.

FIELD OF THE INVENTION

Embodiments of the present invention relate to a method for analyzing the structure of an electrically conductive object.

BACKGROUND TO THE INVENTION

Electrical impedance tomography (EIT) is a known imaging technique, particularly used in medical and other applications for the detection of underlying morphology. Typically, a plurality of electrodes is attached to an object to be imaged. Either input voltages are applied across a subset of 'input' electrodes and output electric currents are measured at 'output' electrodes, or input electric currents are applied between a subset of 'input' electrodes and output voltages are measured at 'output' electrodes or between pairs of output electrodes. For example, when a very small alternating electric current is applied between a subset of 'input' electrodes, the potential difference between output electrodes or between pairs of 'output' electrodes is measured. The current is then applied between a different subset of 'input' electrodes and the potential difference between the output electrodes or between pairs of 'output' electrodes is measured. An electrical impedance image based on variations in electrical impedance can then be constructed using an appropriate image reconstruction technique.

However, the variations of electrical impedance between regions of different morphology may be too small to be discernible.

One approach to this problem has been to perform EIT over a broad range of frequencies. Different morphologies that have an insignificant impedance difference at one frequency may have a more significant difference at a different frequency. However, even using different frequencies the variations of electrical impedance between portions of different morphology may be too small to be discernible.

It is therefore desirable to be able to better differentiate between different morphologies using EIT.

BRIEF DESCRIPTION OF THE INVENTION

According to one embodiment of the invention there is provided a method for analyzing the structure of an electrically conductive object, the method comprising the steps of:
(i) obtaining electrical impedance data for the object;
(ii) analyzing the obtained electrical impedance data using a transfer function of an assumed electrical model to determine a plurality of electrical impedance properties for the object; and
(iii) imaging one or more of the determined electrical impedance properties.

Electrical impedance properties, which are related to the measured electrical impedance data, can be derived from the measured electrical impedance data, and these electrical impedance properties can be used to analyze the structure of the object. However, the amount of variation of the individual electrical impedance properties may be insufficient to enable accurate analysis.

According to one embodiment of the invention there is provided a method for analyzing the structure of an electrically conductive object, the method comprising the steps of:
(i) obtaining electrical impedance data for the object over a range of frequencies;
(ii) analyzing the obtained electrical impedance data using a transfer function of an assumed electrical model to determine a plurality of electrical impedance properties for the object;
(iii) constructively combining selected ones of the determined plurality of electrical impedance properties to provide at least one parametric impedance value for the object; and
(iii) imaging one or more of the determined parametric impedance values.

According to one embodiment of the invention there is provided a method for analyzing the structure of an electrically conductive object, the method comprising the steps of:
(i) obtaining electrical impedance data for the object
(ii) analyzing the obtained electrical impedance data to determine a plurality of electrical impedance properties for the object;
(iii) constructively combining selected electrical impedance properties from said plurality of electrical impedance properties to provide parametric impedance values for the object.

The electrical impedance data for the object may be collected with a frequency bandwidth of between 0 and 100 MHz for biological materials and up to 100 GHz for non-biological conducting materials.

The method may comprise the further step of:
(iv) displaying the parametric impedance values as part of an image from a region of interest (RIO).

Step (iii) may comprise combining predetermined electrical impedance properties according to an impedance emphasizing algorithm.

Step (i) may comprise obtaining electrical impedance data for the object at a plurality of frequencies that depend on the object (bio or non-bio materials). For biological materials it should transfer function is given by the Cole-Cole formula [Cole, 1920; Cole, 1924] over the frequency range 0-100 MHz.

The method may be used to analyze an electrically conductive object having a cellular structure or cell-like structure, and step (ii) may comprise the use of an equivalent electrical impedance circuit to model the structure, such as Cole-Cole model [Cole, 1920; Cole, 1924]

The equivalent electrical impedance circuit may in the limiting case comprise a cell membrane capacitance (C), an intracellular resistance ($R_i$), and an extracellular resistance ($R_e$).

The electrical impedance properties may be selected from the group consisting of $R_i$ (cell/Group intra resistance), $R_e$ (Cell/Group extra resistance), C (Cell/Group capacitance), $f_r$ (cell/group relaxation frequency) and $\alpha$ (cell/group relaxation factor).

Step (iii) may comprise combining $f_r$ (relaxation frequency) and C (cell/group capacitance) by multiplication which may provide parametric impedance values.

BRIEF DESCRIPTION OF THE DRAWINGS

For a better understanding of the present invention reference will now be made by way of example only to the accompanying drawings in which.

DETAILED DESCRIPTION OF EMBODIMENTS OF THE INVENTION

Figure 1:
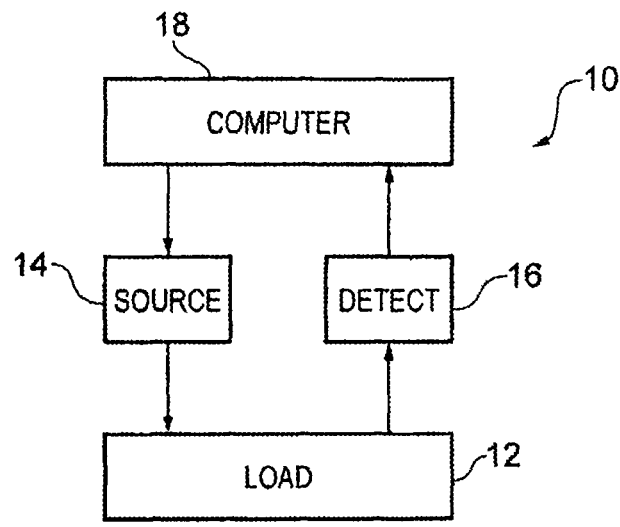
FIG. 1 is a diagrammatic illustration of electrical impedance tomography apparatus.

FIG. 1 illustrates diagrammatically electrical impedance measurement or electrical impedance tomography (EIT) apparatus 10 for measuring impedance data for a load 12. The load 12 comprises an electrically conductive object to which are attached a plurality of electrodes. The term 'electrically conductive' means that the object is capable of conducting an electric current but it does not necessarily need to conduct current very well. The apparatus 10 further comprises a signal source 14, a signal detector 16 and a computer 18. In one embodiment, the signal source provides, as an input signal, an electric current and the signal detector detects, as an output signal, voltage. In another embodiment, the signal source provides, as an input signal, a voltage and the signal detector detects, as an output signal, electric current.

The computer typically comprises at least a processor and a memory. The memory stores a computer program which when loaded into the processor controls the computer.

The input signal is applied using the source 14 to the object via electrodes and the resulting output signals present at same or other electrodes are measured using the detector 16. This process is repeated for different frequencies of input signal. For example, the electric signal may be applied by the signal source 14 at a number of frequencies between 0 Hz (direct current) and 100 MHz, to enable frequency dependent electrical impedance data to be obtained for the object.

The separation of the electrodes used for the impedance measurements determines the resolution or scale at which the object is analyzed. The electrical impedance measurements may be obtained at an expected scale of interest (e.g. micrometer or millimeter range). As an example of the scale of interest, for a biological object, we may be interested in the single cell or in the group cell level or at tissue or histology level, such as lobule or duct in breast tissue. Subsequently the obtained electrical impedance data will be analyzed using a transfer function of an assumed electrical model to determine a plurality of electrical impedance properties for the object. The electrical model used may depend upon the resolution/scale of the impedance measurements.

Figure 2A:
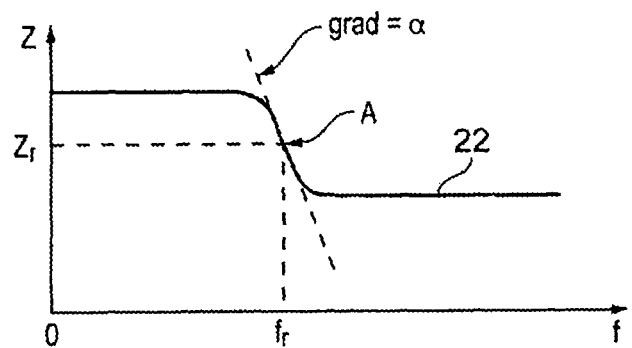
FIGS. 2A and 2B show graphs of measured electrical impedance as a function of frequency with single or multiple dispersion.
Figure 2B:
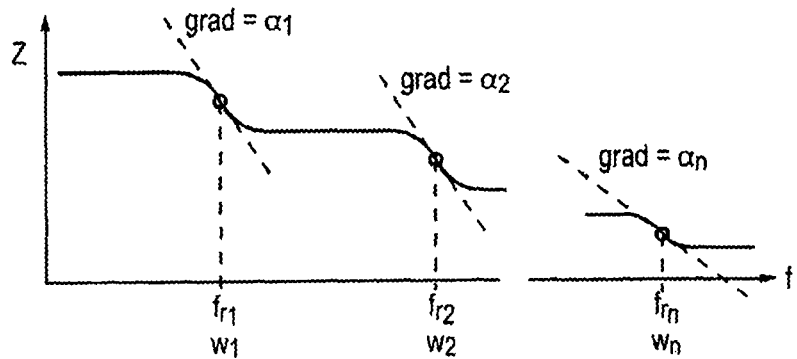

Referring to FIGS. 2A and 2B, the electrical impedance data obtained using the above method can be plotted as a function of frequency. This plot 22 represents the impedance changes vs frequencies or transfer function for the object. The computer 18 is operable to execute an appropriate algorithm to analyze the obtained impedance transfer function or frequency dependent impedance properties and thereby determine a plurality of electrical impedance properties for the object. The electrical impedance properties typically include one or more of:
a) the impedance at the limit $\omega \to 0$ (lower limit)
b) the impedance at the limit $\omega \to \infty$ (upper limit)
c) (i) the relaxation frequency at which there is a change in the impedance (ii) the impedance at that change frequency
(iii) the gradient of the change of impedance, particularly at the relaxation frequencies;

For example, if there are N dispersions including the Alpha, Beta and Gamma dispersions of biological materials [Cole K S, Permeability and impermeability of cell membranes for ions. Cold Spring Harbor Symp. Quant. Biol. 8 pp 110-22, 1940] within the frequency range used, where N>1, then the dispersion frequencies $\omega_1, \omega_2, \ldots \omega_{N-1}, \omega_N$, are identified and the electrical impedance properties for a particular dispersion m would typically include one or more of:
a) For m=1, the impedance at the lower (global) limit $\omega \to 0$
   For m>1, the impedance at the lower (local) limit $\omega \to \omega_m - a$, where $a < (\omega_m - \omega_{m-1})$ and may possibly be $\frac{1}{2}(\omega_m - \omega_{m-1})$
b) For m=N, the impedance at the upper (global) limit $\omega \to \infty$
   For m<N, the impedance at the upper (local) limit $\omega \to \omega_m + b$, where $b < (\omega_{m+1} - \omega_m)$ and may possibly be $b \sim \frac{1}{2}(\omega_{m+1} - \omega_m)$
c) (i) the relaxation frequency $\omega_m(f_m)$ at which there is a change in the impedance
   (ii) the impedance at that change frequency
   (iii) the gradient of the change The amount of variation of one or more of these impedance properties can be used to analyze the structure of the object due to the intra/extra cellular or intra/extra cellular-like related changes.

In some embodiments, the object under analysis is modeled using an equivalent electrical impedance circuit. The object may be modeled using an equivalent electrical impedance circuit 20 illustrated in FIG. 3. Objects which may be modeled using the equivalent electrical impedance circuit 20 may, in a non-limiting example, include human or animal tissue, and porous or other cellular or cellular-like materials.

In the illustrated embodiment, the equivalent electrical impedance circuit 20 comprises a cell portion 21 in parallel with an extra-cell portion 23. The cell portion 21 has a capacitance C and a resistance $R_i$ in series. The resistance C is associated with the cell membrane/boundary and the resistance $R_i$ is associated with the interior of the cell. The extra-cell portion 23 has a resistance $R_e$. The resistance $R_e$ is associated with the structure outside the cell. The resistance $R_e$ is connected in parallel with the series connected capacitance C and resistance $R_i$.

A non-limiting example of a single dispersion impedance transfer function for this circuit is:

$$Z(\omega) = \frac{Re(1 + j \cdot \omega \cdot C \cdot Ri)}{1 + j \cdot \omega \cdot C \cdot (Re + Ri)}$$

In the limit $\omega \to 0$, $Z \to R_e$
In the limit $\omega \to \infty$, $Z \to R_i/R_e$ i.e. $R_i R_e/(R_i + R_e)$
There is a change (dispersion) at frequency fr and an impedance Zr that has a gradient $\alpha$.

The transfer model for multiple dispersion in biological tissue can be modeled by the Cole-Cole equation (Cole K S 1940, Cole K S 1941, McAdams E T et al, 1995) as follows:

$Z = R\infty + (R0 - R\infty)/(1 + (jf/fr))(1-\alpha)$

Usually this equation can be rewritten as the equation below if a three-element electrical equivalent circuit is used for a simple modeling cell suspensions (Fricke and Morse, 1925) or tissues:

$Z = R_e \cdot R_i/(R_e + R_i) + (R_e - R_e \cdot R_i/(R_e + R_i))/(1 + (jf/fr))(1-\alpha)$ Where $R\infty$ is the result of paralleling $R_e$ and $R_i$.

There are changes (dispersion) at frequency $f_{ri}$ and impedance $Z_{ri}$ that has a gradient $\alpha_i$.

As indicated above, the computer 18 is operable to execute an appropriate algorithm to analyze the measured impedance data and extract a plurality of electrical impedance properties for the object under analysis. For example, based on the measured impedance data, the algorithm may be operable to plot impedance data points as a function of frequency and produce a best fit line 22 using the model to form the transfer function illustrated in FIG. 2. From this transfer function, the computer 18 is capable of determining a plurality of individual impedance properties for the object. These impedance properties may include:

a) the impedance at the limit $\omega \to 0$, which gives $R_e$
b) the impedance at the limit $\omega \to \infty$, which gives $R_i R_e/(R_i+R_e)$
c) (i) the relaxation frequency $f_r$ at which there is a change in the impedance
   (ii) the impedance $Z_r$ of the transfer function at that change frequency
   (iii) the gradient $\alpha$ of the change which gives the relaxation factor.

The impedance properties may be used to determine further impedance properties using the model.

For example, if both $R_e$ and $R_i R_e/(R_i+R_e)$ are known then $R_i$ can be determined.

The impedance $Z_r$ of the transfer function at the change (dispersion) frequency $f_r$, is where the capacitor dominates the transfer characteristic as with each small increases in frequency it conducts significantly better reducing the impedance. The impedance $Z_r$ at the change (dispersion) frequency $f_r$, can be modelled as $1/(j \cdot 2\pi \, f_r \cdot C)$. Therefore C can be determined as $1/(j \cdot 2\pi f_r \cdot Z_r)$.

Variations of the individual impedance properties ($R_e$, $R_i$, $f_r$, $Z_r$, $\alpha$, C) may be used to analyze the structure of an object. For example, in the case of human tissue, variations in the individual impedance properties may be indicative of the presence of an abnormality as this gives rise to electrical characteristics which are different to those exhibited by normal, healthy tissue.

However, the amount of variation of the individual impedance properties may be insufficient to enable accurate analysis of the structure. For example, the amount of variation of cell membrane capacitance (C) or relaxation frequency ($f_r$) may be insufficient to be readily detectable, for example in images of the object constructed based on those individual impedance properties.

In embodiments of the invention, selected predetermined impedance properties are 'constructively' combined to provide a parametric impedance value for the object. Constructive combination of the impedance properties in this way to provide parametric impedance value emphasises the variation of the individual electrical impedance properties. This enables the structure of the object to be more accurately analyzed. The parametric impedance value at a particular position may be represented as a pixel value at a corresponding position in an image of the object.

Taking a simple example, if there is a 10% increase in one of the electrical impedance properties, such as cell membrane capacitance (C) from an initial value $C_1$ to $1.1C_1$, and a 10% increase in another of the electrical impedance properties, such as relaxation frequency ($f_r$) from an initial value $f_{r1}$ to $1.1f_{r1}$, these individual 10% increases may be insufficient to be readily detectable, for example discernable in images based on these individual electrical impedance properties. However, combination of these individual electrical impedance properties by multiplication to provide a parametric impedance value will result in a larger increase of 21% ($1.21 f_{r1} C_1$), which is more readily detectable, for example discernible in an image based on the parametric impedance value.

An impedance property may have a positive, neutral or negative correlation with a particular morphology. A positive correlation means its increases, although perhaps not significantly, when the morphology is present. A negative correlation means its decreases, although perhaps not significantly, when the morphology is present. A neutral correlation means it does not change when the morphology is present. An impedance property with a positive correlation can be converted to one with a negative correlation (and visa versa) by taking the inverse.

Constructive combination of impedance properties for detecting a particular morphology means that impedance properties that are correlated in the same sense for that morphology are combined by multiplication (or weighted addition) to create the parametric impedance value and impedance properties that are correlated in the opposite sense for that morphology are combined by division (or weighted subtraction).

Any of the determined impedance properties may be constructively combined in any desired manner to provide a parametric impedance value that has a greater sensitivity to morphological changes that any of the constituent impedance properties. This can be, for example, imaged non-invasively by EIT.

Figure 3:
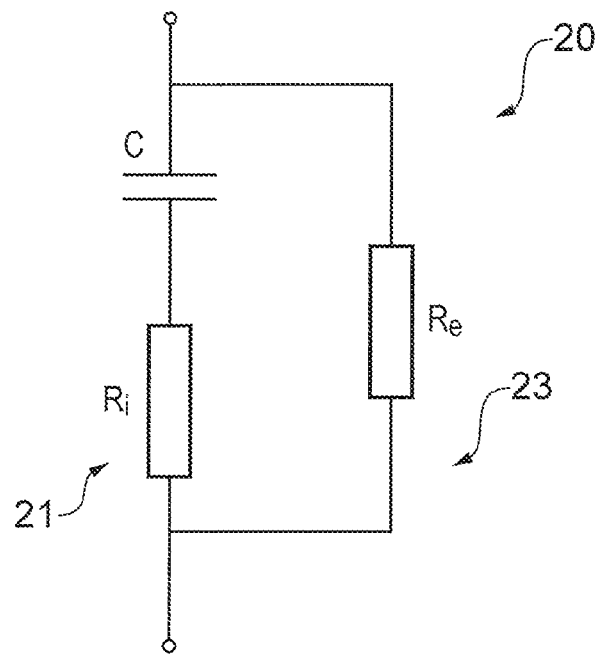
FIG. 3 shows an example electrical impedance circuit model of an object having a cellular or cellular-like structure at the "micro-scale"

Non-limiting examples of the combinations of impedance properties at the limiting level described in FIG. 3:
Combinational Parametric Measurements/2D/3D Imaging (Combined Intra/Extra/Membrane Impedance/Conductivity)
a) Membrane impedance/conductivity and related quantities:
Membrane impedance: $Zm = 1/2\pi r^* fr^* C$
Membrane conductivity: $\sigma m = 2\pi c^* Fr^* C$
b) Combined intracellular impedance/conductivity:
Product: $Ri^*Zm$
  Or: $\sigma i^* \sigma m$
Difference/normalized difference:
  $a^*Ri - b^*Zm$
  Or: $c^*\sigma i - d^*\sigma m$
  Where coefficients a, b, c and d are constant ($-\infty - +\infty$) to be used for match the quantity to be used;
Differential/normalized differential:
  $(a^*Ri - b^*Zm)/Zm$
  Or: $(a^*Ri - b^*Zm)/Ri$
  Alternatively: $(c^*\sigma i - d^*\sigma m)/\sigma m$
  Or: $(c^*\sigma i - d^*cym)/\sigma i$
  Where coefficients a, b, c and d are constant ($-\infty - +\infty$) to be used for match the quantity to be used;
Intra-cellular time constant: $Ri^*C$
  Or: Intra-cellular frequency constant $1/Ri^*C$
c) Combined extra-cellular impedance/Conductivity:
Product: $Re^*Zm$
  Or: $\sigma x^* \sigma m$
Difference/normalized difference:
  $a^*Re - b^*Zm$
  Or: $c^*\sigma x - d^*\sigma m$
  Where coefficients a, b, c and d are constant ($-\infty - +\infty$) to be used for match the quantity to be used;
Differential/normalized differential:
  $(a^*Re - b^*Zm)/Zm$
  Or: $(a^*Re - b^*Zm)/Re$
  Alternatively: $(c^*\sigma x - d^*am)/am$
  Or: $(c^*\sigma x - d^*am)/\sigma x$
Where coefficients a, b, c and d are constant ($-\infty - +\infty$) to be used for match the quantity to be used;
Extra-cellular time constant: $Re^*C$
  Or: Extra-cellular frequency constant $1/Re^*C$ d) Combined extra-to-intra cellular impedance/conductivity:
Product: Re*Ri
  Or: σx*σi
Difference/normalized difference:
  a*Re−b*Ri
  Or: c*σx−d*σi
  Where coefficients a, b, c and d are constant (−∞−+∞) to be used for match the quantity to be used;
Differential/normalized differential:
  (a*Re−b*Ri/Ri
  Or: (a*Re−b*Ri)/Re
  Alternatively: (c*σx−d*ai)/ai
  Or: (c*σx−d*σi)/σx
  Where coefficients a, b, c and d are constant (−∞−+∞) to be used for match the quantity to be used;

Combinational Integrated Cellular Parametric Measurements/2D/3D Imaging with Deviant Dispersion Characteristic ($\alpha$)

For heterogeneous cell groups with mixed with abnormal or other cells, the impedance would demonstrate "flatter" gradient at the dispersion frequency point, a smaller Alpha value. Therefore Alpha has shown the "deviant" or "heterogeneous property" of the tissue or group of cells;

a) "Deviant" membrane impedance/conductivity and related quantities: "Deviant" membrane impedance:
  $\alpha$*Zm
  Or: $\alpha$/Zm
"Deviant" membrane conductivity:
  $\alpha$*Zm
  Or: $\alpha$/Zm
b) Combined "deviant" Infra-cellular impedance/conductivity:
Product: $\alpha$*Ri*Zm
  Or: σi*σm
Difference/normalized difference:
  $\alpha$*(a*Ri−b*Zm)
  Or: a*(c*ai−d*am)
  Where coefficients a, b, c and d are constant (−∞−+∞) to be used for match the quantity to be used;
Differential/normalized differential:
  $\alpha$*($\alpha$*Ri−b*Zm)/Zm
  Or: $\alpha$*(a*Ri−b*Zm)/Ri
  Alternatively: $\alpha$*(c*σi−d*σm)/σm
  Or: $\alpha$*(c*σi−d*σm)/σi
  Where coefficients a, b, c and d are constant (−∞−+∞) to be used for match the quantity to be used;
Intra-cellular time constant: $\alpha$*(Ri*C)
  Or: Intra-cellular frequency constant $\alpha$*(1/Ri*C)
c) Combined extra-cellular impedance/conductivity:
Product: $\alpha$*Re*Zm
  Or: $\alpha$*σx*σm
Difference/normalized difference:
  $\alpha$*(a*Re−b*Zm)
  Or: $\alpha$*(c*σx−d*σm)
  Where coefficients a, b, c and d are constant (−∞−+∞) to be used for match the quantity to be used;
Differential/normalized differential:
  $\alpha$*(a*Re−b*Zm)/Zm
  Or: $\alpha$*(a*Re−b*Zm)/Re
  Alternatively: $\alpha$*(c*σx−d*σm)/σm
  Or: $\alpha$*(c*σx−d*σm)/σx
  Where coefficients a, b, c and d are constant (−∞−+∞) to be used for match the quantity to be used;
Extra-cellular time constant: $\alpha$*Re*C
  Or: Extra-cellular frequency constant $\alpha$*(1/Re*C)
d) Combined extra-to-intra cellular impedance/conductivity:
Product: $\alpha$*Re*Ri
  Or: $\alpha$*σx*σi
Difference/normalized difference:
  $\alpha$*(a*Re−b*Ri)
  Or: $\alpha$*(c*σx−d*σi)
  Where coefficients a, b, c and d are constant (−∞−+∞) to be used for match the quantity to be used;
Differential/normalized differential:
  $\alpha$*(a*Re−b*Ri)/Ri
  Or: $\alpha$*(a*Re−b*Ri)/Re
  Alternatively: $\alpha$*(c*σx−d*σi)/σi
  Or: $\alpha$*(c*σx−d*σi)/σx
  Where coefficients a, b, c and d are constant (−σ−+∞) to be used for match the quantity to be used;

A suitable impedance emphasizing algorithm may be implemented by the computer 18 to select the optimum electrical impedance properties for combination and their manner of combination to maximize the variation of the resultant parametric impedance values.

After the parametric impedance value has been obtained for the object, in some embodiments the parametric impedance value is displayed as part of a parametric image of the structure of the object, and abnormalities in the structure of the object are thus emphasized and more readily discernible in the image. The structure of the object can therefore be more readily determined by analysis of the image.

Figure 4:
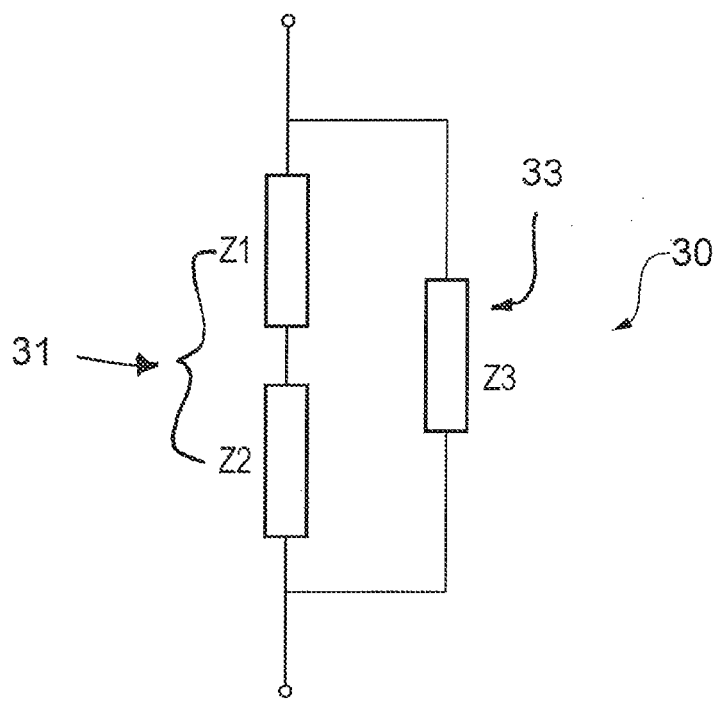
FIG. 4 shows a generic electrical impedance circuit model of an object having a cellular or cellular-like structure at a "macro-scale".

FIG. 4 illustrates a more generic model of the object under analysis. In the illustrated embodiment, the equivalent electrical impedance circuit 30 comprises an inclusion portion 31 in parallel with an inter-inclusion portion 33. The inclusion portion 31 has impedance Z1 and impedance Z2 in series. The impedance Z1 may be associated with the inclusion boundary (may be representative of the membrane related components of a group of cells) and the impedance Z2 may associated with the interior of the inclusion (may be representative of the intra-cellular related components of a group of cells). The inter-inclusion portion 33 has impedance Z3. The impedance Z3 is associated with the structure outside the inclusion (may be representative of extracellular components of a group of cells). The impedance Z3 is connected in parallel with the series connected impedance Z1 and Z2.

The impedance transfer function for this circuit is:

$$Z(\omega) = \frac{Z1 \cdot Z2 \cdot Z3}{Z1 \cdot Z2 + Z1 \cdot Z3 + Z2 \cdot Z3}$$

Non-limiting examples of the combinations of impedance properties at the level described in FIG. 4:

Combinational Parametric Measurements/2D/3D Imaging
a) Inclusion boundary impedance/conductivity and related quantities:
Inclusion boundary impedance: $Zm = \frac{1}{2\pi} \cdot fr \cdot Z2$
Inclusion boundary conductivity: σm=2π*Fr*Z2
b) Combined Intra-inclusion impedance/conductivity:
Product: Z1*Zm
  Or: σ1*σm
Difference/normalized difference:
  a*Z1−b*Zm
  Or: c*σ1−d*σm
  Where coefficients a, b, c and d are constant (−∞−+∞) to be used for match the quantity to be used;
Differential/normalized differential:
  (a*Z1−b*Zm)/Zm
  Or: (a*Z1−b*Zm)/Z1
  Alternatively: (c*σ1−d*σm)/σm
  Or: (c*σ1−d*σm)/σ1

Where coefficients a, b, c and d are constant ($-\infty$–$+\infty$) to be used for match the quantity to be used;
Intra-inclusion time constant: $Z1*Z2$
　Or: Intra-inclusion frequency constant$1/Z1*Z2$
c) Combined inter-inclusion impedance/conductivity:
Product: $Z3*Zm$
　Or: $\sigma3*\sigma m$
Difference/normalized difference:
　$a*Z3-b*Zm$
　Or: $c*\sigma3-d*\sigma m$
　Where coefficients a, b, c and d are constant ($-\infty$–$+\infty$) to be used for match the quantity to be used;
d) Combined inter-to-intra inclusion impedance/conductivity:
Product: $Re*Ri$
　Or: $\sigma x*\sigma i$
Difference/normalized difference:
　$a*Re-b*Ri$
　Or: $c*\sigma x-d*\sigma i$
　Where coefficients a, b, c and d are constant ($-\infty$–$+\infty$) to be used for match the quantity to be used;
Differential/normalized differential:
　$(a*Re-b*Ri)/Ri$
　Or: $(a*Re-b*Ri)/Re$
　Alternatively: $(c*\sigma x-d*\sigma i)/\sigma i$
　Or: $(c*\sigma x-d*\sigma i)/\sigma x$
Where coefficients a, b, c and d are constant ($-\infty$–$+\infty$) to be used for match the quantity to be used;
Differential/normalized differential:
　$(a*Z3-b*Zm)/Zm$
　Or: $(a*Z3-b*Zm)/Z3$
　Alternatively: $(c*\sigma3-d*\sigma m)/\sigma m$
　Or: $(c*\sigma3-d*\sigma m)/\sigma3$
Where coefficients a, b, c and d are constant ($-\infty$–$+\infty$) to be used for match the quantity to be used;
Inter-inclusion time constant: $Z3*Z2$
　Or: Inter-inclusion frequency constant$1/Z3*Z2$
　Combinational Integrated Parametric Measurements/2D/3D Imaging with Deviant Dispersion Characteristic ($\alpha$)

For heterogeneous groups with mixed inclusions, the impedance would demonstrate "flatter" gradient at the dispersion frequencies, a smaller Alpha value. Therefore Alpha has shown the "deviant" or "heterogeneous property" of the macro-scale object;
a) "Deviant" inclusion boundary impedance/conductivity and related quantities:
"Deviant" inclusion boundary impedance:
　$\alpha*Zm$
　Or: $\alpha/Zm$
"Deviant" inclusion boundary conductivity:
　$\alpha*\sigma m$
　Or: $\alpha/\sigma m$
b) Combined "deviant" Intra-inclusion impedance/conductivity:
Product: $\alpha*Z1*Zm$
　Or: $\sigma1*\sigma m$
Difference/normalised difference:
　$\alpha*(a*Z1-b*Zm)$
　Or: $\alpha*(c*\sigma1-d*\sigma m)$
　Where coefficients a, b, c and d are constant ($-\infty$–$+\infty$) to be used for match the quantity to be used;
Differential/normalised differential:
　$\alpha*(a*Z1-b*Zm)/Zm$
　Or: $\alpha*(a*Z1-b*Zm)/Z1$
　Alternatively: $\alpha*(c*\sigma1-d*\sigma m)/\sigma m$
　Or: $\alpha*(c*\sigma1-d*\sigma m)/\sigma1$ Where coefficients a, b, c and d are constant ($-\infty$–$+\infty$) to be used for match the quantity to be used;
Intra-inclusion time constant: $\alpha*(Z1*Z2)$
　Or: Intra-inclusion frequency constant $\alpha*(1/Z1*Z2)$
c) Combined inter-inclusion impedance/conductivity:
Product: $\alpha*Z3*Zm$
　Or: $\sigma3*\sigma m$
Difference/normalised difference:
　$\alpha*(a*Z3-b*Zm)$
　Or: $\alpha*(c*\sigma3-d*\sigma m)$
　Where coefficients a, b, c and d are constant ($-\infty$–$+\infty$) to be used for match the quantity to be used;
Differential/normalised differential:
　$\alpha*(a*Z3-b*Zm)/Zm$
　Or: $\alpha*(a*Z3-b*Zm)/Z3$
　Alternatively: $\alpha*(c*\sigma3-d*\sigma m)/\sigma m$
　Or: $\alpha*(c*\sigma3-d*\sigma m)/\sigma3$
　Where coefficients a, b, c and d are constant ($-\infty$–$+\infty$) to be used for match the quantity to be used;
Inter-inclusion time constant: $\alpha*Z3*Z2$
　Or: Inter-inclusion frequency constant $\alpha*(1/Z3*Z2)$
d) Combined inter-to-intra inclusion impedance/conductivity:
Product: $\alpha*Re*Ri$
　Or: $\alpha*\sigma x*\sigma i$
Difference/normalised difference:
　$\alpha*(a*Re-b*Ri)$
　Or: $\alpha*(c*\sigma x-d*\sigma i)$
Where coefficients a, b, c and d are constant ($-\infty$–$+\infty$) to be used for match the quantity to be used;
Differential/normalised differential:
　$\alpha*(a*Re-b*Ri)/Ri$
　Or: $\alpha*(a*Re-b*Ri)/Re$
　Alternatively: $\alpha*(c*\sigma x-d*\sigma i)/\sigma i$
　Or: $\alpha*(c*\sigma x-d*\sigma i)/\sigma x$
Where coefficients a, b, c and d are constant ($-\infty$–$+\infty$) to be used for match the quantity to be used;

This model is a fractal model as previously described in U.S. Pat. No. 6,856,824. Each of the impedances Z1, Z2, Z3 may be represented using either the circuit 30 or at the limiting level where Z1 is equivalent to R1, Z2 is equivalent to C and Z3 in equivalent to Re. The term 'fractal' is used to express the fact that at whatever level of dimension one looks at the structure the model is the same.

Although embodiments of the present invention have been described in the preceding paragraphs with reference to various non-limiting examples, it should be appreciated that modifications to the examples given can be made without departing from the scope of the invention as claimed. As an example, the method may be used in the food industry to check the quality of food, particularly meat.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A method for analyzing the structure of an electrically conductive object, the method comprising the steps of:
　(i) obtaining electrical impedance data for the object over a range of frequencies;
　(ii) analyzing the obtained electrical impedance data using a transfer function of an assumed electrical model to determine a plurality of electrical impedance properties for the object;

(iii) constructively combining selected ones of the determined plurality of electrical impedance properties to provide at least one parametric impedance value for the object; and (iii) imaging one or more of the determined parametric impedance values.

2. A method according to claim 1, wherein the electrical model assumes first and second serially connected impedances connected in parallel with a third impedance.

3. A method according to claim 1, wherein the electrical model assumes a capacitor and a serially connected resistor, which are connected in parallel with another resistor.

4. A method according to claim 1, wherein the electrical model is a fractal model and is usable at any resolution.

5. A method according to claim 1, wherein the electrical impedance properties are selected from the group comprising:
 an impedance at a lower frequency limit,
 an impedance at an upper frequency limit,
 a relaxation frequency $f_r$ at which there is a change in the impedance,
 an impedance at that relaxation frequency, and
 the impedance gradient at that relaxation frequency.

6. A method according to claim 1, wherein the electrical model assumes a capacitance and a serially connected resistance, which are connected in parallel with a parallel resistance to form a model circuit having a relaxation frequency, wherein the parametric impedance value used for imaging is a combination of two or more of: the capacitance, the relaxation frequency, the serial resistance and the parallel resistance.

7. A method according to claim 1, wherein the electrical model assumes a 'membrane' capacitance and a serially connected intracellular resistance, which are connected in parallel with an extracellular resistance, wherein the parametric impedance value used for imaging includes one of:
 Membrane impedance
 Membrane conductivity
 Intracellular impedance product
 Intracellular impedance difference
 Intracellular impedance normalized difference
 Intracellular impedance differential
 Intracellular impedance normalized differential
 Intracellular conductivity product
 Intracellular conductivity difference
 Intracellular conductivity normalized difference
 Intracellular conductivity differential
 Intracellular conductivity normalized differential
 Intracellular time constant
 Intracellular frequency constant
 Extracellular impedance product
 Extracellular impedance difference
 Extracellular impedance normalized difference
 Extracellular impedance differential
 Extracellular impedance normalized differential
 Extracellular conductivity product
 Extracellular conductivity difference
 Extracellular conductivity normalized difference
 Extracellular conductivity differential
 Extracellular conductivity normalized differential
 Extracellular time constant
 Extracellular frequency constant
 Extra-intra impedance product
 Extra- intra impedance difference
 Extra-intra impedance normalized difference
 Extra-intra differential
 Extra-intra normalized differential
 Extra-intra conductivity product
 Extra-intra conductivity difference
 Extra-intra conductivity normalized difference
 Extra-intra conductivity differential
 Extra-intra conductivity normalized differential any one of the preceding parameters modified by a dispersion gradient $\alpha$.

8. A method according to claim 1, wherein the electrical model assumes a first impedance and a serially connected second impedance, which are connected in parallel with a third impedance to form a model circuit having a relaxation frequency, wherein the parametric impedance value used for imaging is a combination of two or more of: the first impedance, the relaxation frequency, the second impedance and the third impedance.

9. A method according to claim 1, wherein the electrical model assumes an inclusion boundary impedance and a serially connected intra-inclusion impedance, which are connected in parallel with an inter-inclusion impedance, wherein the parametric impedance value used for imaging includes one of:
 inclusion boundary impedance
 inclusion boundary conductivity
 Intra-inclusion impedance product
 Intra-inclusion impedance difference
 Intra-inclusion impedance normalized difference
 Intra-inclusion impedance differential
 Intra-inclusion impedance normalized differential
 Infra-inclusion conductivity product
 Intra-inclusion conductivity difference
 Intra-inclusion conductivity normalized difference
 Infra-inclusion conductivity differential
 Intra-inclusion conductivity normalized differential
 Intra-inclusion time constant
 Intra-inclusion frequency constant
 Inter-inclusion impedance product
 Inter-inclusion impedance difference
 Inter-inclusion impedance normalized difference
 Inter-inclusion impedance differential
 Inter-inclusion impedance normalized differential
 Inter-inclusion conductivity product
 Inter-inclusion conductivity difference
 Inter-inclusion conductivity normalized difference
 Inter-inclusion conductivity differential
 Inter-inclusion conductivity normalized differential
 Inter-inclusion time constant
 Inter-inclusion frequency constant
 Inter-intra impedance product
 Inter-intra impedance difference
 Inter-intra impedance normalized difference
 Inter-intra differential
 Inter-intra normalized differential
 Inter-intra conductivity product
 Inter-intra conductivity difference
 Inter-intra conductivity normalized difference
 Inter-intra conductivity differential
 Inter-intra conductivity normalized differential any one of the preceding parameters modified by a dispersion gradient $\alpha$.

10. A method as claimed in claim 1 wherein the frequency range is between 0 and 100 MHz.

11. A method as claimed in claim 1, wherein the frequency range is between 0 and 100 GHz.

12. A method for analyzing the structure of an electrically conductive object, the method comprising the steps of:
 (i) obtaining electrical impedance data for the object over a frequency range;

(ii) analyzing the obtained electrical impedance data to determine a plurality of electrical impedance properties for the object;
(iii) constructively combining selected electrical impedance properties from said plurality of electrical impedance properties to provide parametric impedance values for the object.

13. A method according to claim 12, wherein the method comprises the further step of:
(iv) displaying the parametric impedance values as part of an image.

14. A method according to claim 12, wherein step (iii) comprises constructively combining predetermined electrical impedance properties according to an impedance emphasizing algorithm.

15. A method according to claim 12, wherein step (i) comprises obtaining electrical impedance data for the object at a plurality of frequencies.

16. A method according to claim 12, wherein the method is used to analyze an electrically conductive object having a cellular structure, and step (ii) comprises the use of an equivalent electrical impedance circuit to model the cellular structure.

17. A method according to claim 16, wherein the equivalent electrical impedance circuit comprises a cell membrane capacitance (C) in series with an intracellular resistance ($R_i$), the cell membrane capacitance (C) and intracellular resistance ($R_i$) being in parallel with an extracellular resistance ($R_e$) or an equivalent electrical circuit.

18. A method according to claim 12, wherein the electrical impedance properties are selected from the group consisting of $R_i$ (intracellular resistance), $R_e$ (extracellular resistance), C (membrane capacitance), $f_r$ (relaxation frequency) and α (relaxation time).

19. A method according to claim 18, wherein step (iii) comprises combining $f_r$ (relaxation frequency) and C (membrane capacitance) by multiplication to provide a parametric impedance value.

20. A method for analyzinq the structure of an electrically conductive object, the method comprising the steps of:
obtaining electrical impedance data for the object;
(ii) analyzinq the obtained electrical impedance data using a transfer function of an assumed electrical model to determine a plurality of electrical impedance properties for the object; and
(iii) imaging one or more of the determined electrical impedance properties.

* * * * *

UNITED STATES PATENT AND TRADEMARK OFFICE
CERTIFICATE OF CORRECTION

PATENT NO.        : 8,594,780 B2
APPLICATION NO.   : 12/451944
DATED             : November 26, 2013
INVENTOR(S)       : Wei Wang It is certified that error appears in the above-identified patent and that said Letters Patent is hereby corrected as shown below:

In the Claims

At column 12, line 29, claim 9, line 14, remove the word "Infra-inclusion" and replace with --Intra-inclusion--.

At column 12, line 32, claim 9, line 17, remove the word "Infra-inclusion" and replace with --Intra-inclusion--.

Signed and Sealed this
Thirteenth Day of May, 2014

Michelle K. Lee
*Deputy Director of the United States Patent and Trademark Office*